US009393376B2

(12) United States Patent
Inoue et al.

(10) Patent No.: US 9,393,376 B2
(45) Date of Patent: Jul. 19, 2016

(54) AIRWAY ADAPTOR AND BIOLOGICAL INFORMATION ACQUIRING SYSTEM (71) Applicant: NIHON KOHDEN CORPORATION, Tokyo (JP)

(72) Inventors: Masayuki Inoue, Tokyo (JP); Yoshinobu Ono, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 187 days.

(21) Appl. No.: 13/768,514

(22) Filed: Feb. 15, 2013

(65) Prior Publication Data

US 2013/0231540 A1  Sep. 5, 2013

(30) Foreign Application Priority Data

Mar. 5, 2012  (JP) ................ 2012-048223

(51) Int. Cl.
*A61B 5/097* (2006.01)
*A61B 5/01* (2006.01)
(Continued)

(52) U.S. Cl.
CPC ............. *A61M 16/0666* (2013.01); *A61B 5/01* (2013.01); *A61B 5/082* (2013.01); *A61B 5/097* (2013.01); *A61B 5/14552* (2013.01); *A61B 5/682* (2013.01); *A61B 5/6819* (2013.01); *A61M 16/0057* (2013.01); *A61M 16/0488* (2013.01); *A61M 16/085* (2014.02);
(Continued)

(58) Field of Classification Search
CPC .. A61B 5/14551; A61B 5/6819; A61B 5/682; A61B 5/08; A61B 5/082; A61B 5/0833; A61B 5/0836; A61B 5/0873; A61B 5/0878; A61B 5/097; A61M 6/0666
See application file for complete search history.

(56) References Cited

U.S. PATENT DOCUMENTS 5,335,659 A  8/1994  Pologe
5,957,127 A  9/1999  Yamamori et al.
(Continued)

FOREIGN PATENT DOCUMENTS

CN  1646054 A  7/2005
CN  101432036 A  5/2009
(Continued)

OTHER PUBLICATIONS

Extended European Search Report for the related European Patent Application No. 13156802.4 dated Aug. 29, 2013.
(Continued)

*Primary Examiner* — Charles A Marmor, II
*Assistant Examiner* — Thaddeus Cox
(74) *Attorney, Agent, or Firm* — Pearne & Gordon LLP (57) ABSTRACT An airway adaptor includes: an airway case including a gas passage, the airway case adapted to be attachable to a part of a carbon dioxide sensor configured to detect a concentration of carbon dioxide contained in exhalation, flowing into the gas passage, of the subject, the exhalation; a nasal cannula having a pair of insertion portions inserted into nostrils of the subject to guide exhalation from the nostrils to the gas passage; a mouth guide placed in front of a mouth of the subject to guide exhalation from the mouth to the gas passage; a light-emitting element supported by one of the insertion portions; and a light-receiving element supported by the other of the insertion portions. When the insertion portions are inserted into the nostrils, the light-emitting element and the light-receiving element are opposed to each other across a nasal septum of the subject.

8 Claims, 11 Drawing Sheets (51) Int. Cl.
*A61M 16/06* (2006.01)
*A61B 5/1455* (2006.01)
*A61B 5/08* (2006.01)
*A61B 5/00* (2006.01)
*A61M 16/00* (2006.01)
*A61M 16/04* (2006.01)
*A61M 16/08* (2006.01)
*A61B 5/083* (2006.01)

(52) U.S. Cl.
CPC ........... *A61M 16/0858* (2014.02); *A61B 5/083* (2013.01); *A61M 2230/205* (2013.01)

(56) References Cited

U.S. PATENT DOCUMENTS

| | | | |
|---|---|---|---|
| 6,909,912 | B2 | 6/2005 | Melker |
| 7,024,235 | B2 | 4/2006 | Melker et al. |
| 7,445,602 | B2 | 11/2008 | Yamamori et al. |
| 7,455,644 | B2 | 11/2008 | Yamamori et al. |
| 7,462,154 | B2 | 12/2008 | Yamamori et al. |
| 2003/0236452 | A1 | 12/2003 | Melker et al. |
| 2004/0206907 | A1 | 10/2004 | Yamamori et al. |
| 2004/0230108 | A1 | 11/2004 | Melker et al. |
| 2004/0260161 | A1 | 12/2004 | Melker et al. |
| 2005/0107709 | A1 | 5/2005 | Hampel et al. |
| 2006/0042631 | A1* | 3/2006 | Martin et al. ............ 128/207.18 |
| 2006/0247551 | A1 | 11/2006 | Yamamori et al. |
| 2007/0027375 | A1* | 2/2007 | Melker et al. ................. 600/340 |
| 2007/0027376 | A1 | 2/2007 | Todokoro et al. |
| 2007/0236452 | A1 | 10/2007 | Venkatesh et al. |
| 2008/0058621 | A1 | 3/2008 | Melker et al. |
| 2008/0190436 | A1 | 8/2008 | Jaffe et al. |
| 2009/0069646 | A1 | 3/2009 | Yamamori et al. |
| 2011/0094513 | A1 | 4/2011 | Takatori et al. |
| 2012/0078069 | A1 | 3/2012 | Melker |
| 2012/0209096 | A1 | 8/2012 | Jaffe et al. |
| 2012/0248985 | A1* | 10/2012 | Lin et al. ....................... 315/117 |
| 2013/0013281 | A1* | 1/2013 | Orr et al. ......................... 703/11 |
| 2014/0094669 | A1 | 4/2014 | Jaffe et al. |
| 2014/0094670 | A1 | 4/2014 | Melker et al. |
| 2014/0155704 | A1 | 6/2014 | Melker et al. |
| 2014/0155713 | A1 | 6/2014 | Melker et al. |
| 2014/0158132 | A1 | 6/2014 | Melker |
| 2014/0180026 | A1 | 6/2014 | Melker et al. |

FOREIGN PATENT DOCUMENTS

| | | |
|---|---|---|
| CN | 101516300 A | 8/2009 |
| EP | 1 804 872 A2 | 7/2007 |
| JP | 8-233806 A | 9/1996 |
| JP | 2007-54594 A | 3/2007 |
| JP | 2007-518480 A | 7/2007 |
| JP | 2009-172347 A | 8/2009 |
| JP | 2011-115543 A | 6/2011 |

OTHER PUBLICATIONS

Japanese Office Action for the related Japanese Patent Application No. 2012-048223 dated Aug. 4, 2015.

Chinese Office Action for the related Chinese Patent Application No. 201310059852.3 dated Nov. 30, 2015.

Japanese Office action for Application No. 2012-048223 dated Mar. 22, 2016.

* cited by examiner

AIRWAY ADAPTOR AND BIOLOGICAL INFORMATION ACQUIRING SYSTEM

CROSS-REFERENCE TO RELATED APPLICATION(S)

This application is based upon and claims the benefit of priority from prior Japanese patent application No. 2012-048223, filed on Mar. 5, 2012, the entire contents of which are incorporated herein by reference.

BACKGROUND

The presently disclosed subject matter relates to an airway adaptor which is attached to the face of the subject to collect the exhalation, and also to a system for acquiring various kinds of biological information by using the airway adaptor.

There is a system for acquiring the concentration of carbon dioxide contained in the exhalation of the subject, as an example of biological information. JP-A-8-233806 discloses a biological information acquiring system in which light-emitting and light-receiving elements that function as a part of a carbon dioxide sensor are attached to an airway adaptor. A gas passage provided in the airway adaptor extends so as to cross the space between the light-emitting and light-receiving elements, and the exhalation of the subject directly flows into the gas passage.

The light-emitting element emits light which is absorbed by carbon dioxide (for example, infrared light). The intensity of light which reaches the light-receiving element differs depending on the concentration of carbon dioxide contained in the exhalation of the subject. When a signal which is output from the light-receiving element, and which corresponds to the intensity is monitored, therefore, it is possible to acquire the concentration of the carbon dioxide.

As another example of biological information, there is a system for acquiring the arterial oxygen saturation (SpO2) of the subject. The arterial oxygen saturation is an index indicating the amount of oxygen which is supplied into the blood. JP-A-2007-54594 discloses a biological information acquiring system in which light-emitting and light-receiving elements that function as a part of an arterial oxygen saturation sensor are opposed to each other across the fingertip of the subject.

The light-emitting element emits red and infrared light beams. The intensities of light beams which reach the light-receiving element differ depending on the ratio of hemoglobin combined with oxygen in the blood. When a signal which is output from the light-receiving element, and which corresponds to the intensities is monitored, therefore, it is possible to acquire the arterial oxygen saturation.

A further example of biological information to be acquired is the respiratory volume of the subject. As a method of acquiring the respiratory volume, there is a method in which a tube connected to a pressure sensor is attached to the nostril or mouth of the subject, and a pressure variation in the tube which is produced by respiration is detected by the pressure sensor.

As described above, in order to acquire various kinds of biological information, devices which correspond to respective kinds of biological information, such as a sensor element and a tube must be attached to various places of the body of the subject. Therefore, the attaching work requires much labor, and the subject to whom many devices are attached feels strong botheration.

SUMMARY

The presently disclosed subject matter may provide a technique in which, in the case where a plurality of kinds of biological information are to be acquired, the work of attaching devices to the subject can be efficiently performed, and botheration that is felt by the subject can be suppressed.

There is provided an airway adaptor which is adapted to be attached to a face of a subject, the airway adaptor comprising: an airway case which includes a gas passage, the airway case adapted to be attachable to a part of a carbon dioxide sensor configured to detect a concentration of carbon dioxide contained in exhalation of the subject, the exhalation flowing into the gas passage; a nasal cannula having a pair of insertion portions which are adapted to be inserted respectively into nostrils of the subject to guide exhalation from the nostrils to the gas passage when the airway adaptor is attached to the face; a mouth guide adapted to be placed in front of a mouth of the subject to guide exhalation from the mouth to the gas passage when the airway adaptor is attached to the face; a light-emitting element supported by one of the pair of insertion portions; and a light-receiving element supported by the other of the pair of insertion portions, wherein when the pair of insertion portions are inserted into the nostrils of the subject, the light-emitting element and the light-receiving element are opposed to each other across a nasal septum of the subject.

At least a part of the pair of insertion portions may be elastically deformable, the part being to be opposed to the nasal septum.

The nasal cannula may include a branch gas passage which is configured to guide a pressure generated by the exhalation from the nostrils to a pressure sensor.

There is also provided a biological information acquiring system comprising: an airway case which is adapted to be attached to a face of a subject, and which includes a gas passage; a carbon dioxide sensor which is attached to the airway case, and which is configured to detect a concentration of carbon dioxide contained in exhalation of the subject, the exhalation flowing into the gas passage; an arterial oxygen saturation sensor which is configured to detect an arterial oxygen saturation of the subject; a nasal cannula having a pair of insertion portions which are adapted to be inserted respectively into nostrils of the subject to guide exhalation from the nostrils to the gas passage when the airway case is attached to the face; a mouth guide adapted to be placed in front of a mouth of the subject to guide exhalation from the mouth to the gas passage when the airway case is attached to the face; a light-emitting element supported by one of the pair of insertion portions; and a light-receiving element supported by the other of the pair of insertion portions, wherein when the pair of insertion portions are inserted into the nostrils of the subject, the light-emitting element and the light-receiving element are opposed to each other across a nasal septum of the subject to operate as a part of the arterial oxygen saturation sensor.

The biological information acquiring system may further include a pressure sensor, and the nasal cannula may include a branch gas passage which is configured to guide a pressure generated by the exhalation from the nostrils to the pressure sensor.

The light-receiving element may operate as a part of a temperature sensor.

There is also provided a biological information acquiring system comprising: a pressure sensor; an arterial oxygen saturation sensor configured to detect an arterial oxygen saturation of a subject; a nasal cannula having: a pair of insertion portions which are adapted to be inserted respectively into nostrils of the subject; and a gas passage which is configured to guide a pressure generated by exhalation from the nostrils to the pressure sensor; a light-emitting element supported by an interior of one of the pair of insertion portions; and a light-receiving element supported by an interior of the other of the pair of insertion portions, wherein when the pair of insertion portions are inserted into the nostrils of the subject, the light-emitting element and the light-receiving element are opposed to each other across a nasal septum of the subject to operate as a part of the arterial oxygen saturation sensor, and at least a part of the pair of insertion portions is formed as an elastically deformable portion, the part being to be opposed to the nasal septum.

There is also provided a biological information acquiring system comprising: a carbon dioxide sensor configured to detect a concentration of carbon dioxide contained in exhalation of a subject; an arterial oxygen saturation sensor configured to detect an arterial oxygen saturation of the subject; a nasal cannula having: a pair of insertion portions which are adapted to be inserted respectively into nostrils of the subject; and a gas passage which is configured to guide a pressure generated by exhalation from the nostrils to the carbon dioxide sensor; a light-emitting element supported by an interior of one of the pair of insertion portions; and a light-receiving element supported by an interior of the other of the pair of insertion portions, wherein when the pair of insertion portions are inserted into the nostrils of the subject, the light-emitting element and the light-receiving element are opposed to each other across a nasal septum of the subject to operate as a part of the arterial oxygen saturation sensor, and at least a part of the pair of insertion portions is formed as an elastically deformable portion, the part being to be opposed to the nasal septum.

DETAILED DESCRIPTION OF EXEMPLARY EMBODIMENTS

Hereinafter, embodiments of the presently disclosed subject matter will be described in detail with reference to the accompanying drawings. In the drawings which will be referenced in the following description, the scale is adequately changed in order to draw components in a recognizable size.

Figure 1:
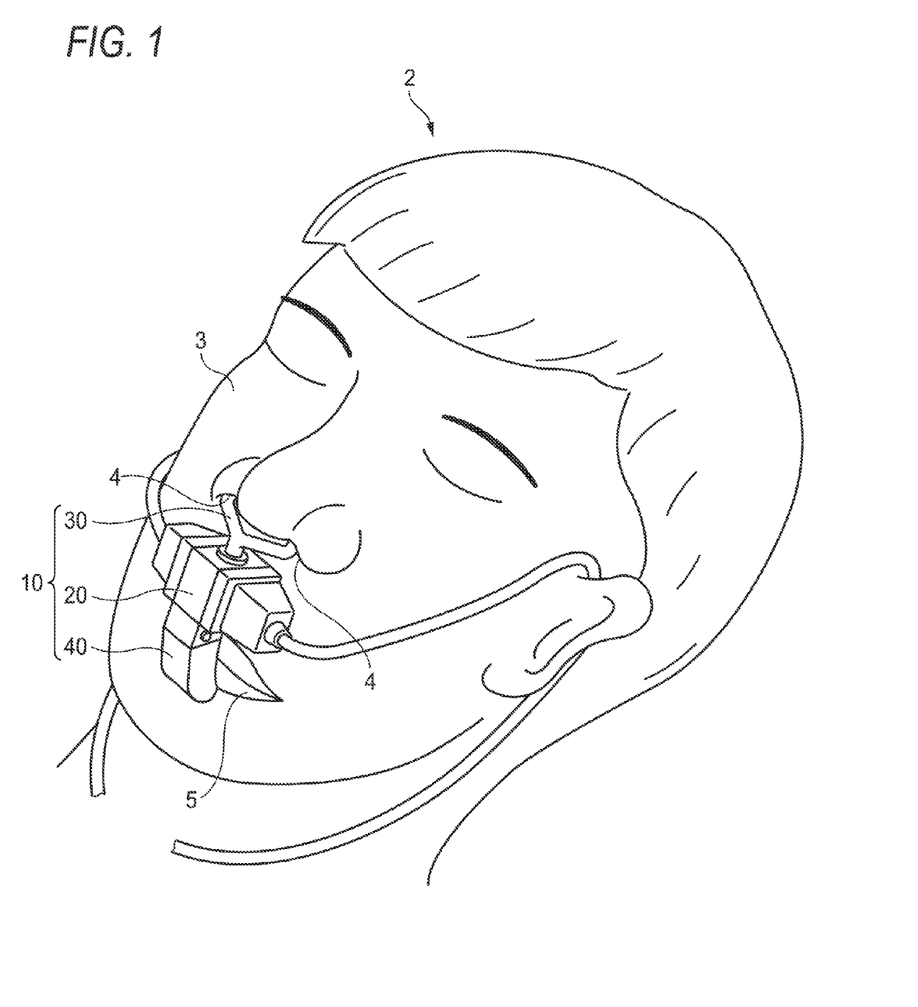
FIG. 1 is a perspective view illustrating a state where an airway adaptor of a first embodiment of the presently disclosed subject matter is attached to the face of the subject.

FIG. 1 shows a state where an airway adaptor 10 of a biological information acquiring system 11 of a first embodiment of the presently disclosed subject matter is attached to the face 3 of the subject 2. The airway adaptor 10 includes an airway case 20, a nasal cannula 30, and a mouth guide 40.

Figure 2:
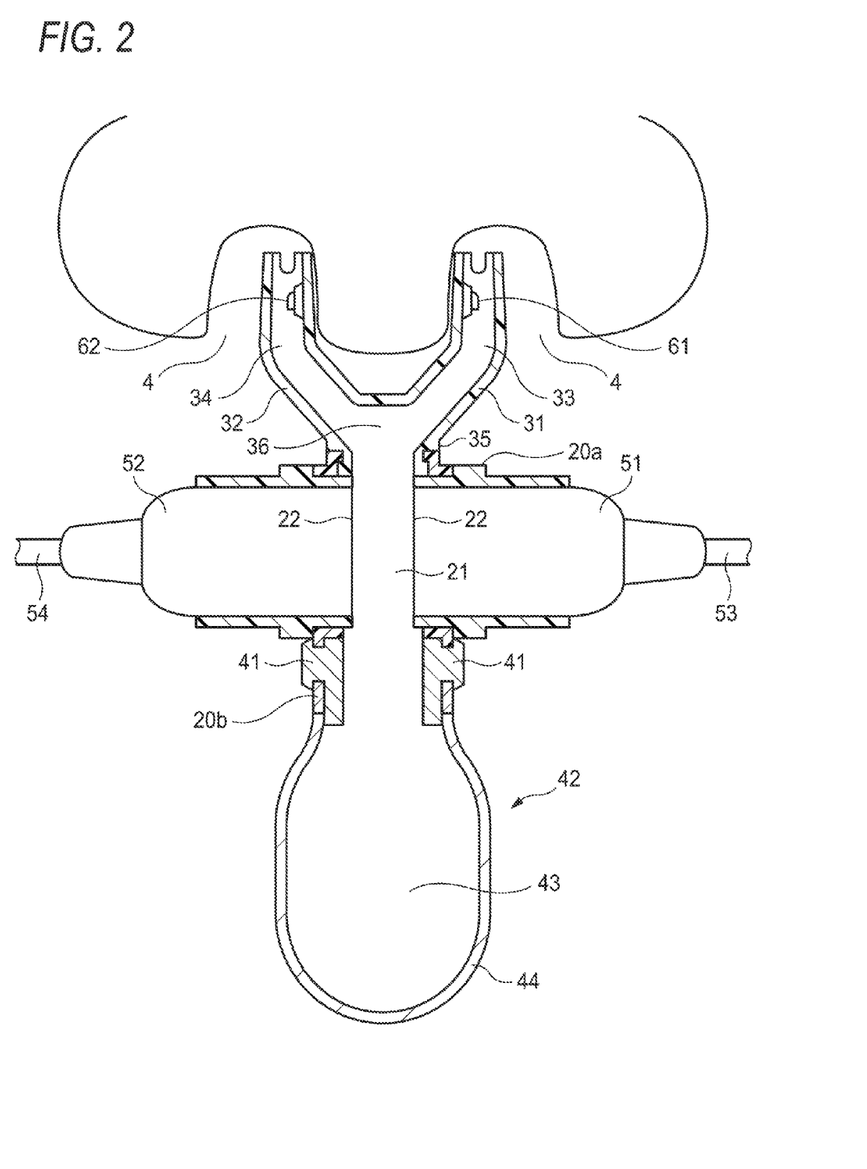
FIG. 2 is a longitudinal sectional view illustrating the internal configuration of the airway adaptor of FIG. 1.

As shown in FIG. 2, a first light-emitting element 51 and a first light-receiving element 52 are detachably attached to the airway case 20. In the embodiment, the first light-emitting element 51 is a light-emitting diode, and the first light-receiving element 52 is a photodiode.

A gas passage 21 which extends so as to cross the space between the first light-emitting element 51 and the first light-receiving element 52 is formed in the airway case 20. A part of the gas passage 21 is partitionedly formed by a pair of antifog films 22. When the first light-emitting element 51 and the first light-receiving element 52 are attached to the airway case 20, the light-emitting surface of the first light-emitting element, and the light-receiving surface of the first light-receiving element are opposed to the respective antifog films 22.

The nasal cannula 30 is made of a soft material such as silicone rubber or elastomer, and has a pair of insertion portions 31, 32. The interiors of the insertion portions 31, 32 are formed as hollow gas passages 33, 34, respectively, and, in a basal end portion 35, form a confluent portion 36. The basal end portion 35 is fixed to the upper surface 20a of the airway case 20, and the confluent portion 36 communicates with the gas passage 21 through an opening which is formed in the upper surface 20a of the airway case 20.

When the airway adaptor 10 is attached to the face 3 of the subject 2, the pair of insertion portions 31, 32 are inserted into the nostrils 4 of the subject 2. The exhalation from the nostrils 4 is guided to the gas passage 21 of the airway case 20 through the gas passages 33, 34 and the confluent portion 36.

The mouth guide 40 is swingably supported through a support shaft 41 in a lower portion 20b of the airway case 20. An inner space 43 which is partitionedly formed by a dome-like body portion 42 communicates with the gas passage 21 through an opening which is formed in the lower portion 20b of the airway case 20.

When the airway adaptor 10 is attached to the face 3 of the subject 2, the body portion 42 of the mouth guide 40 is placed in front of the mouth 5 of the subject 2. The exhalation from the mouth 5 is guided to the gas passage 21 through the inner space 43. When the body portion 42 is swung in the antero-posterior direction about the support shaft 41, the position of a peripheral portion 44 of the body portion 42 with respect to the mouth 5 of the subject 2 can be adjusted. The distance between the peripheral portion 44 and the mouth 5 is adequately adjusted so that an appropriate volume of the exhalation is guided to the gas passage 21.

Figure 4:
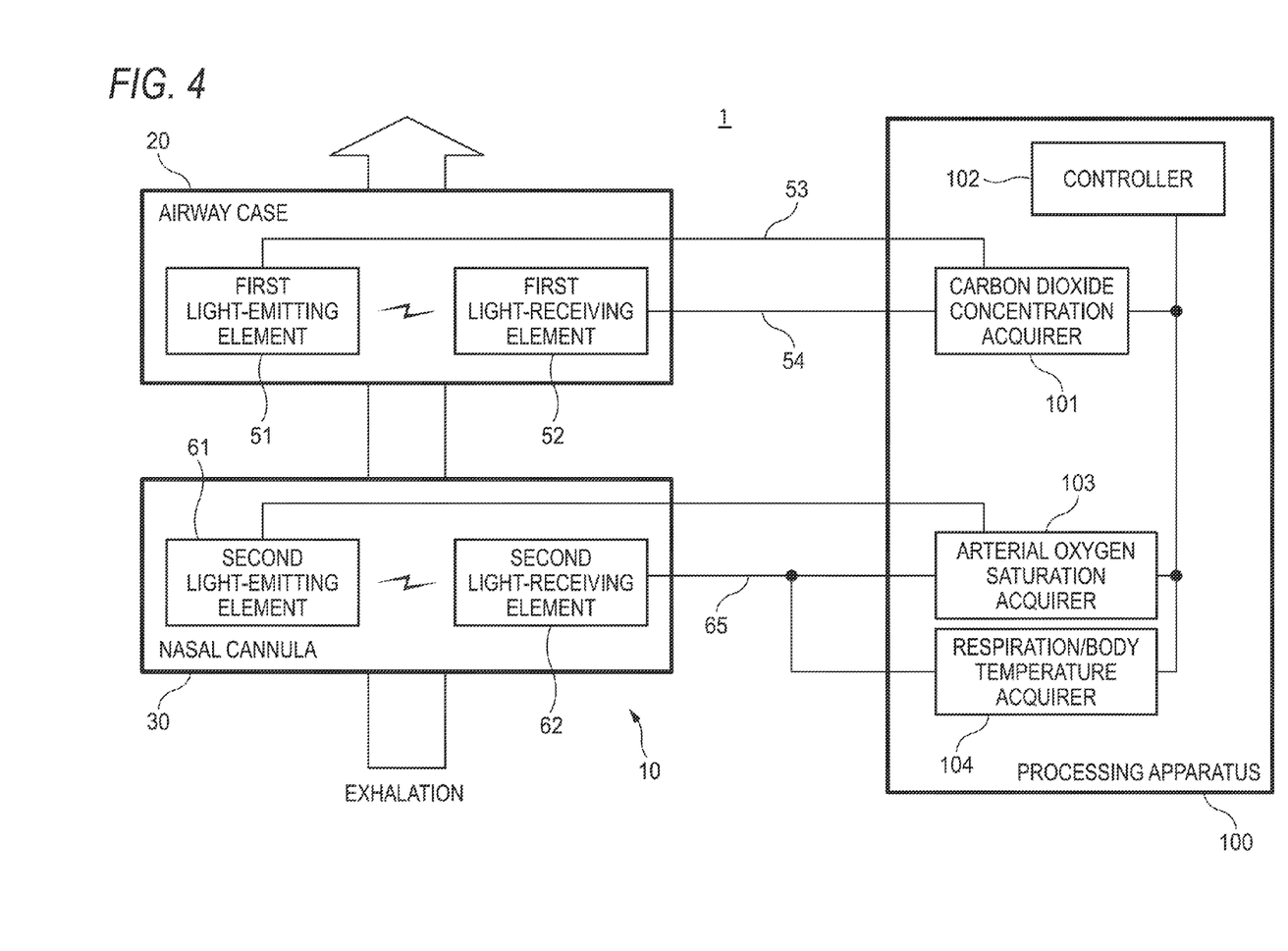
FIG. 4 is a functional block diagram illustrating the configuration of a biological information acquiring system of the first embodiment of the presently disclosed subject matter.

FIG. 4 is a functional block diagram illustrating the configuration of a biological information acquiring system 1 of the embodiment. The first light-emitting element 51 and the first light-receiving element 52 are communicably connected to a carbon dioxide concentration acquirer 101 of a processing apparatus 100 through lead wires 53, 54, respectively. The carbon dioxide concentration acquirer 101 is communicably connected to a controller 102.

In accordance with instructions from the controller 102, the carbon dioxide concentration acquirer 101 outputs a light-emitting signal. The light-emitting signal is supplied to the first light-emitting element 51 through the lead wire 53, and a light beam (infrared light beam) having a predetermined wavelength is emitted from the first light-emitting element 51.

The light beam emitted from the first light-emitting element 51 propagates across the gas passage 21 to be received by the first light-receiving element 52. The first light-receiving element 52 is configured so as to output an output signal corresponding to the intensity of the received light, to the lead wire 54.

When the exhalation from at least one of the nostrils 4 and mouth 5 of the subject 2 is guided to the gas passage 21 of the airway case 20, the concentration of carbon dioxide in the gas passage 21 is increased. Then, the received-light intensity of the first light-receiving element 52 is lowered, and also the state of the output signal is changed. The carbon dioxide concentration acquirer 101 monitors the state of the output signal through the lead wire 54, so that the concentration of carbon dioxide contained in the exhalation of the subject 2 can be acquired as biological information.

Namely, the first light-emitting element 51, the first light-receiving element 52, the lead wires 53, 54, and the carbon dioxide concentration acquirer 101 function as the carbon dioxide sensor in the presently disclosed subject matter.

As shown in FIG. 2, the airway adaptor 10 of the embodiment further includes a second light-emitting element 61 and a second light-receiving element 62. The second light-emitting element 61 is a light-emitting diode, and the first light-receiving element 62 is a photodiode. When the insertion portions 31, 32 of the nasal cannula 30 are inserted into the nostrils 4 of the subject 2, the second light-emitting element 61 and the second light-receiving element 62 are opposed to each other across the nasal septum 4a of the subject 2.

The second light-emitting element 61 is placed in the gas passage 33 of the one insertion portion 31 of the nasal cannula 30. The second light-receiving element 62 is placed in the gas passage 32 of the other insertion portion 32 of the nasal cannula 30. As enlargedly shown in FIG. 3, the second light-emitting element 61 and the second light-receiving element 62 are supported by the insertion portions 31, 32 through a support member 63, respectively.

Figure 3:
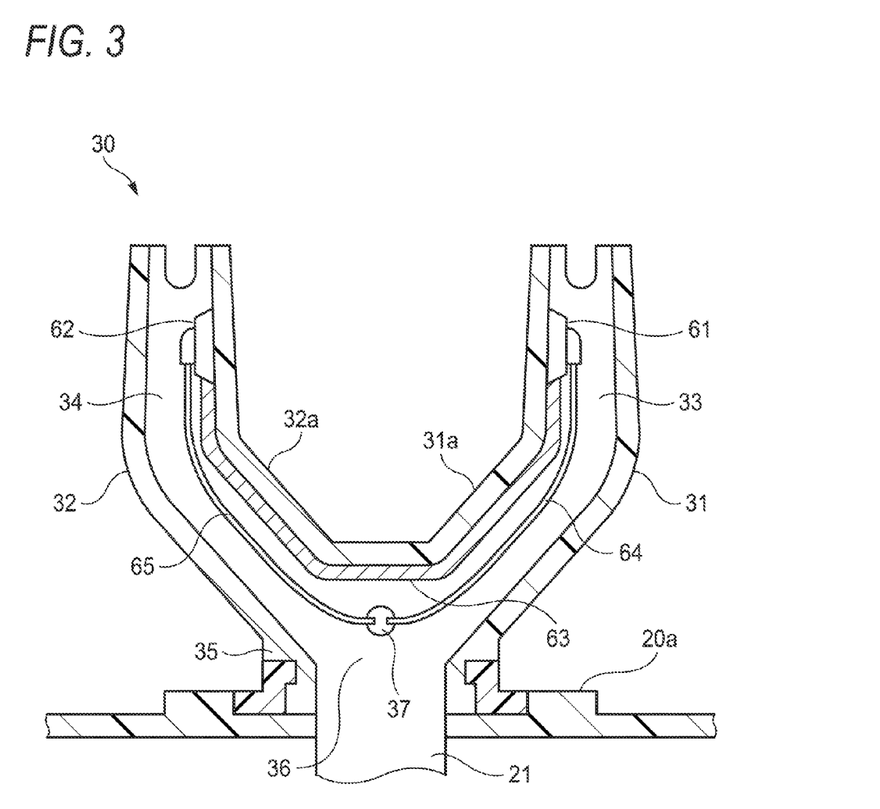
FIG. 3 is a longitudinal sectional view enlargedly illustrating the internal configuration of a nasal tube of the airway adaptor of FIG. 1.

The support member 63 is a wire which extends along the inner walls of portions 31a, 32a of the insertion portions 31, 32 which are opposed to the nasal septum 4a. The second light-emitting element 61 and the second light-receiving element 62 are supported in end portions of the support member, respectively.

The support member 63 is formed by a material which is plastically deformable. Therefore, the member is deformed by application of a force, and, when the force application is cancelled, maintains the deformed shape. Namely, the support member 63 causes the portions 31a, 32a which are in the pair of insertion portions 31, 32, and which are opposed to the nasal septum 4a, to function as a plastically deformable portion.

As shown in FIG. 4, the second light-emitting element 61 and the second light-receiving element 62 are communicably connected to an arterial oxygen saturation acquirer 103 of the processing apparatus 100 through lead wires 64, 65, respectively. The arterial oxygen saturation acquirer 103 is communicably connected to the controller 102.

As shown in FIG. 3, the lead wires 64, 65 extend along the gas passages 33, 34 of the nasal cannula 30, and are drawn to the outside through a draw-out port 37 formed in the basal end portion 35. The draw-out port 37 functions also as a ventilation port of the nasal cannula 30.

In accordance with instructions from the controller 102, the arterial oxygen saturation acquirer 103 outputs a light-emitting signal. The light-emitting signal is supplied to the second light-emitting element 61 through the lead wire 64, and light beams (red and infrared light beams) each having a predetermined wavelength are emitted from the second light-emitting element 61.

The light beams emitted from the second light-emitting element 61 transmit through the nasal septum 4a to be received by the second light-receiving element 62. The second light-receiving element 62 is configured so as to output an output signal corresponding to the intensities of the respective wavelength light beams, to the lead wire 65.

The intensities of the respective wavelength light beams which reach the second light-receiving element 62 differ depending on the ratio of hemoglobin combined with oxygen in the blood flowing blood vessels in the nasal septum 4a, and therefore also the state of the output signal is changed. The arterial oxygen saturation acquirer 103 monitors the state of the output signal through the lead wire 65, so that the arterial oxygen saturation can be acquired as biological information through a calculation process.

Namely, the second light-emitting element 61, the second light-receiving element 62, the lead wires 64, 65, and the arterial oxygen saturation acquirer 103 function as the arterial oxygen saturation sensor in the presently disclosed subject matter.

As shown in FIG. 4, the second light-receiving element 62 is communicably connected to a respiration/body temperature acquirer 104 of the processing apparatus 100 through the lead wire 65. The second light-receiving element 62 has characteristics in which, when the ambient temperature is raised, the dark current is increased. Each time when the exhalation from the nostrils 4 passes through the gas passage 34 of the nasal cannula 30, the dark current is increased with increase in temperature. The respiration/body temperature acquirer 104 monitors the value of the dark current through the lead wire 65, so that at least one of the respiratory condition and body temperature of the subject 2 can be acquired as biological information.

Namely, the second light-receiving element 62, the lead wire 65, and the respiration/body temperature acquirer 104 function as the temperature sensor in the presently disclosed subject matter.

The respiration/body temperature acquirer 104 is communicably connected to the controller 102. As required, the various kinds of biological information which are acquired by the carbon dioxide concentration acquirer 101, the arterial oxygen saturation acquirer 103, and the respiration/body temperature acquirer 104 are stored in a storage apparatus (not shown) and/or displayed on a display apparatus (not shown), by the controller 102.

According to the configuration of the embodiment, the placement of the first light-emitting element 51 and first light-receiving element 52 which operate as a part of the carbon dioxide sensor, and that of the second light-emitting element 61 and second light-receiving element 62 which operate as apart of the arterial oxygen saturation sensor are completed simply by attaching the airway adaptor 10 to the face 3 of the subject 2. Namely, the first light-emitting element 51 and the first light-receiving element 52 are placed between the nostrils 4 and the mouth 5, and the second light-emitting element 61 and the second light-receiving element 62 are opposed to each other across the nasal septum 4a.

Therefore, it is not necessary to attach the carbon dioxide sensor and the arterial oxygen saturation sensor to respective separate places of the body of the subject 2. Consequently, the labor of the attaching work can be saved, and botheration felt by the subject 2 can be suppressed.

The second light-receiving element 62 can further operate as a part of the temperature sensor. Therefore, the respiratory condition and body temperature of the subject 2 can be acquired as biological information without involving labor and botheration of attaching an additional sensor.

In the embodiment, furthermore, the portions 31a, 32a which are in the pair of insertion portions 31, 32, and which are opposed to the nasal septum 4a are caused by the support member 63 to function as a plastically deformable portion. Therefore, the support member 63 can be plastically deformed so as to extend along the shape of the surface of the nasal septum 4a, by applying a force to the insertion portions 31, 32 of the nasal cannula 30 in the state where the second light-emitting element 61 and the second light-receiving element 62 are opposed to each other across the nasal septum 4a. Even after the force application is cancelled, the support member 63 maintains the deformed shape, and therefore the second light-emitting element 61 and the second light-receiving element 62 can be prevented from being separated from the nasal septum 4a. According to the configuration, the accuracy of the measurement of the arterial oxygen saturation can be enhanced. Next, an airway adaptor 10A of a biological information acquiring system 1A of a second embodiment of the presently disclosed subject matter will be described with reference to FIGS. 5 to 8. The components which are identical, similar, or equivalent to those of the airway adaptor 10 of the biological information acquiring system 1 of the first embodiment are denoted by the same reference numerals, and duplicated description is omitted.

Figure 8:
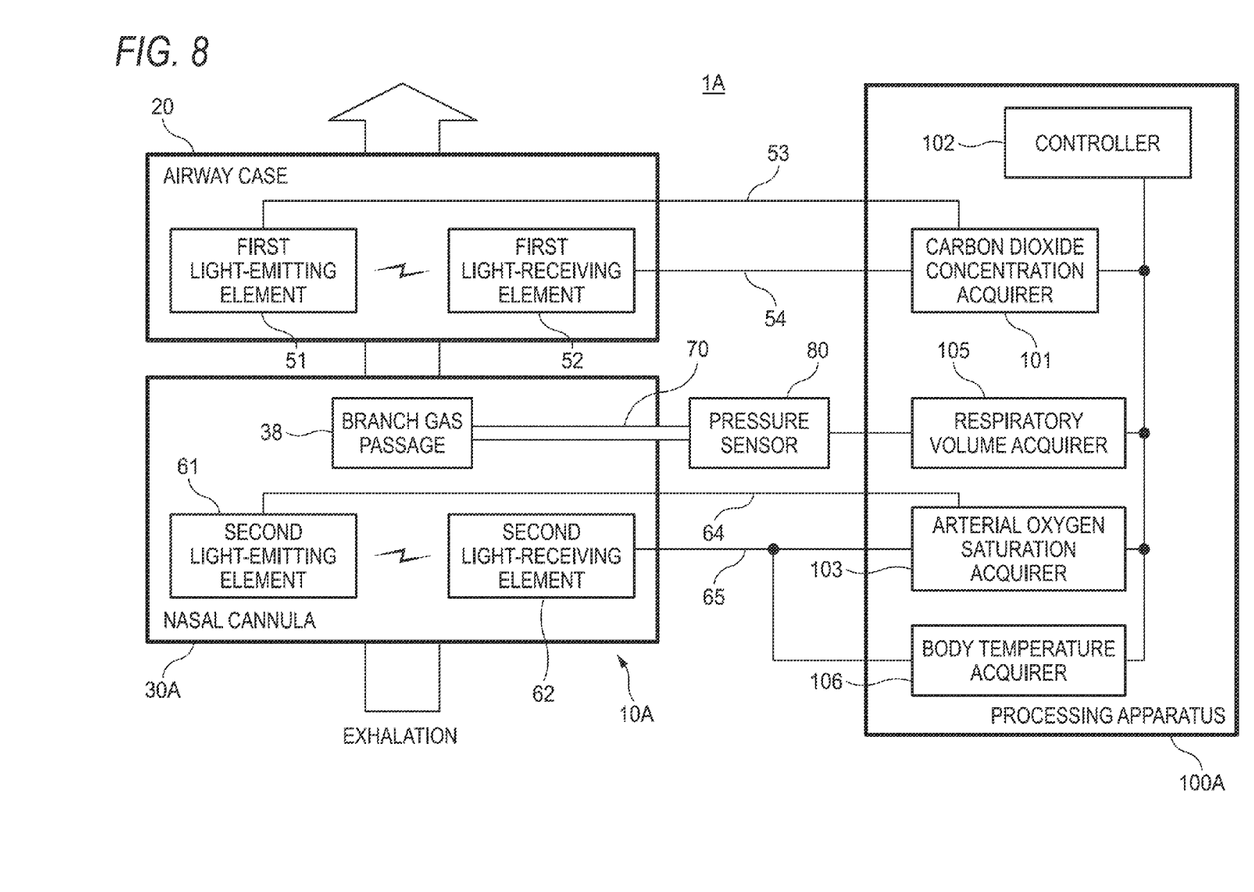
FIG. 8 is a functional block diagram illustrating the configuration of a biological information acquiring system of the second embodiment of the presently disclosed subject matter.

As shown in the functional block diagram of FIG. 8, the biological information acquiring system 1A of the embodiment is different from the biological information acquiring system 1 of the first embodiment in that a part of a nasal cannula 30A of the airway adaptor 10A is connected to a pressure sensor 80 through branch gas passages 38, and a processing apparatus 100A includes a respiratory volume acquirer 105 and a body temperature acquirer 106.

Figure 5:
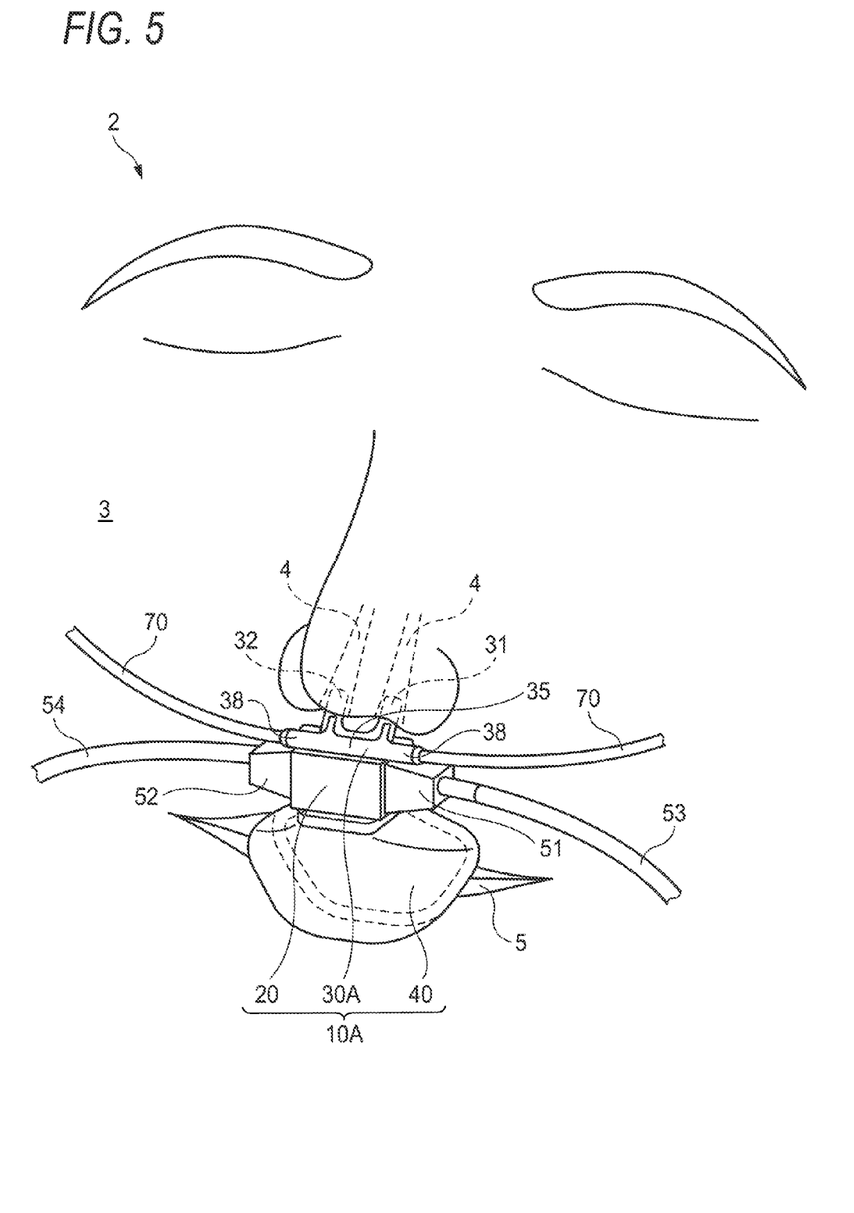
FIG. 5 is a perspective view illustrating a state where an airway adaptor of a second embodiment of the presently disclosed subject matter is attached to the face of the subject.
Figure 6:
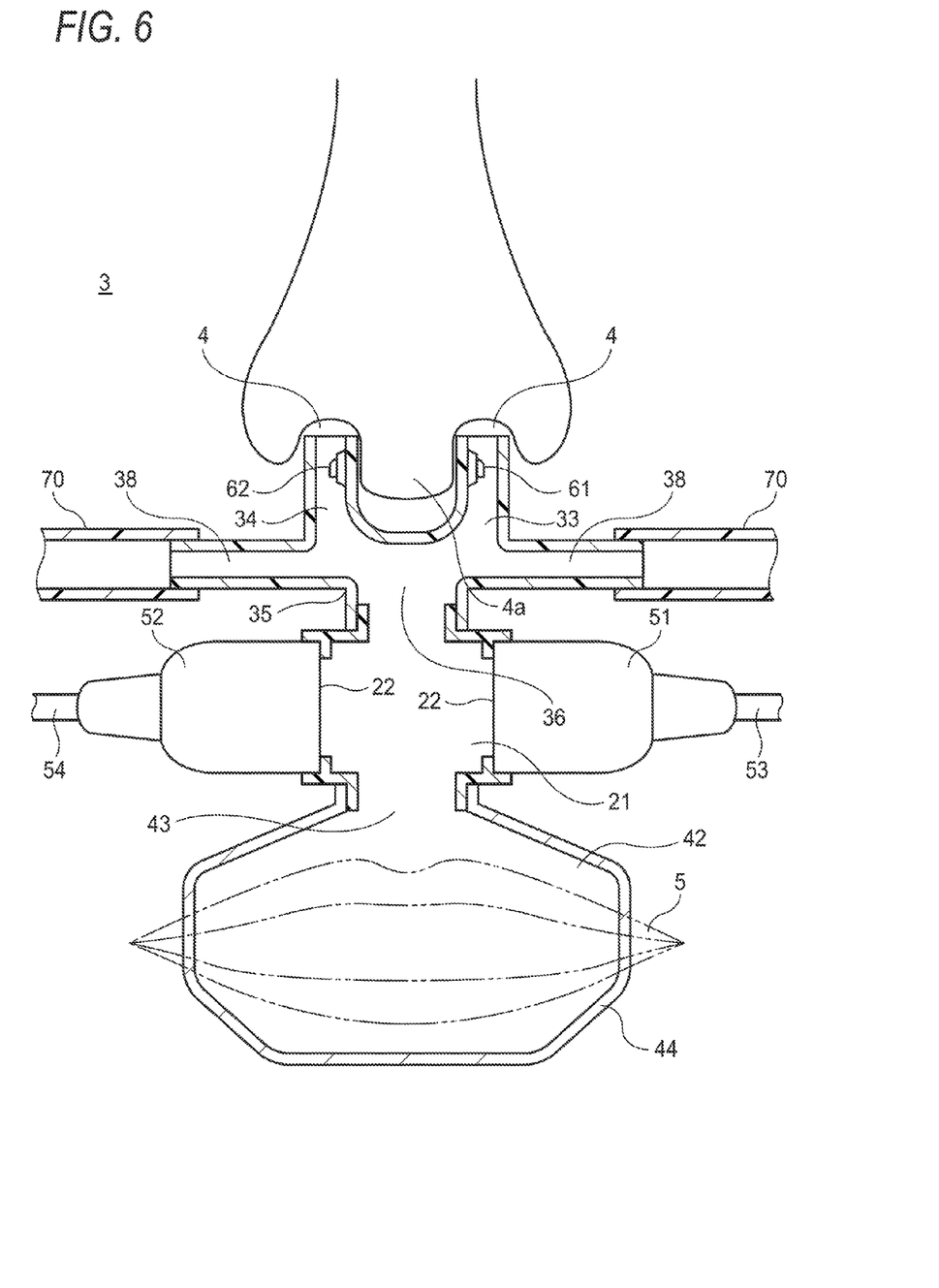
FIG. 6 is a longitudinal sectional view illustrating the internal configuration of the airway adaptor of FIG. 5
Figure 7:
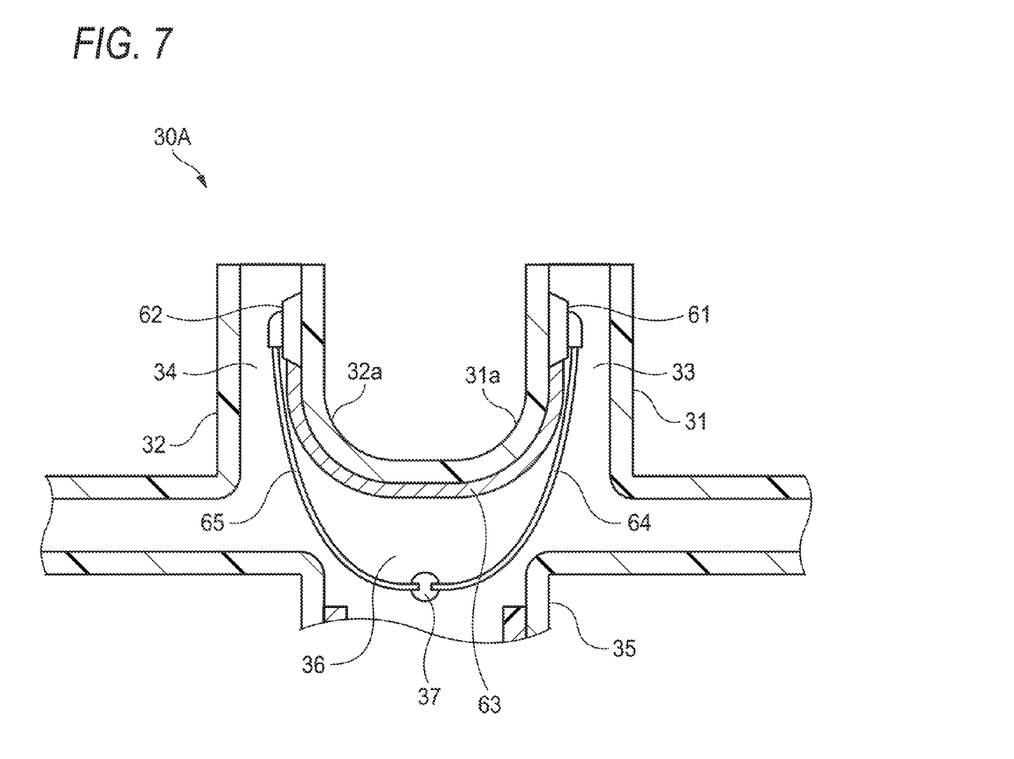
FIG. 7 is a longitudinal sectional view enlargedly illustrating the internal configuration of a nasal tube of the airway adaptor of FIG. 5.

As shown in FIG. 5, the nasal cannula 30A of the airway adaptor 10A of the embodiment is different from the airway adaptor 10 of the first embodiment in that the branch gas passages 38 which extend in the lateral direction are disposed in front of the basal end portion 35 of the pair of insertion portions 31, 32. As shown in FIG. 6, the branch gas passages 38 communicate with the gas passages 33, 34 which are formed in the respective interiors of the insertion portions 31, 32, in the confluent portion 36.

Tubes 70 made of vinyl are detachably attached to the tip ends of the branch gas passages 38, respectively. As shown in FIG. 8, the tubes 70 are connected to the pressure sensor 80. Part of the exhalation from the nostrils 4 of the subject 2 is guided to the pressure sensor 80 through the tubes 70 via the branch gas passages 38. The pressure sensor 80 is configured so as to detect the pressure variation which is caused in the tubes 70 by the passage of the exhalation, and output a signal corresponding to the pressure value.

As shown in FIG. 8, the pressure sensor 80 is communicably connected to the respiratory volume acquirer 105 of the processing apparatus 100A. The respiratory volume acquirer 105 monitors the output signal of the pressure sensor 80 to perform a process, whereby the respiratory condition and volume of the subject 2 can be acquired as biological information.

Since information related to the respiratory condition can be acquired by the pressure sensor 80 and the respiratory volume acquirer 105, the output signal of the second light-receiving element 62 functioning as a part of the temperature sensor is used for acquiring the body temperature of the subject 2 as biological information by the body temperature acquirer 106.

The respiratory volume acquirer 105 and the body temperature acquirer 106 are communicably connected to the controller 102. The various kinds of biological information which are acquired by the carbon dioxide concentration acquirer 101, the arterial oxygen saturation acquirer 103, the respiratory volume acquirer 105, and the body temperature acquirer 106 are caused as required to be stored in the storage apparatus (not shown) and/or displayed on the display apparatus (not shown), by the controller 102.

According to the configuration of the embodiment, also the respiratory volume of the subject 2 can be further acquired as biological information simply by attaching the airway adaptor 10A to the face 3 of the subject 2. Since the exhalation of the subject 2 for acquiring the respiratory volume is guided to the pressure sensor through the branch gas passages 38 which are formed as a part of the nasal cannula 30A, labor and botheration of attaching an additional sensor are not involved.

Figure 9:
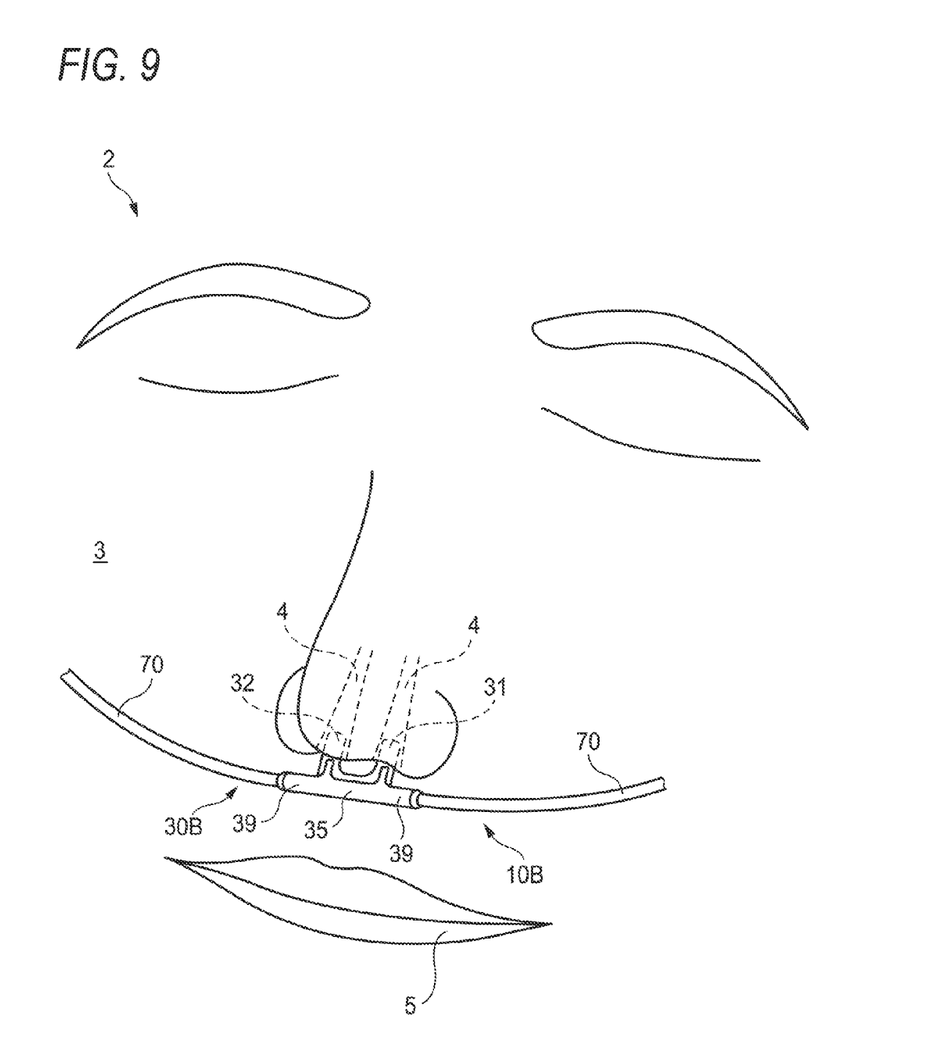
FIG. 9 is a perspective view illustrating a state where an airway adaptor of a third embodiment of the presently disclosed subject matter is attached to the face of the subject.
Figure 10:
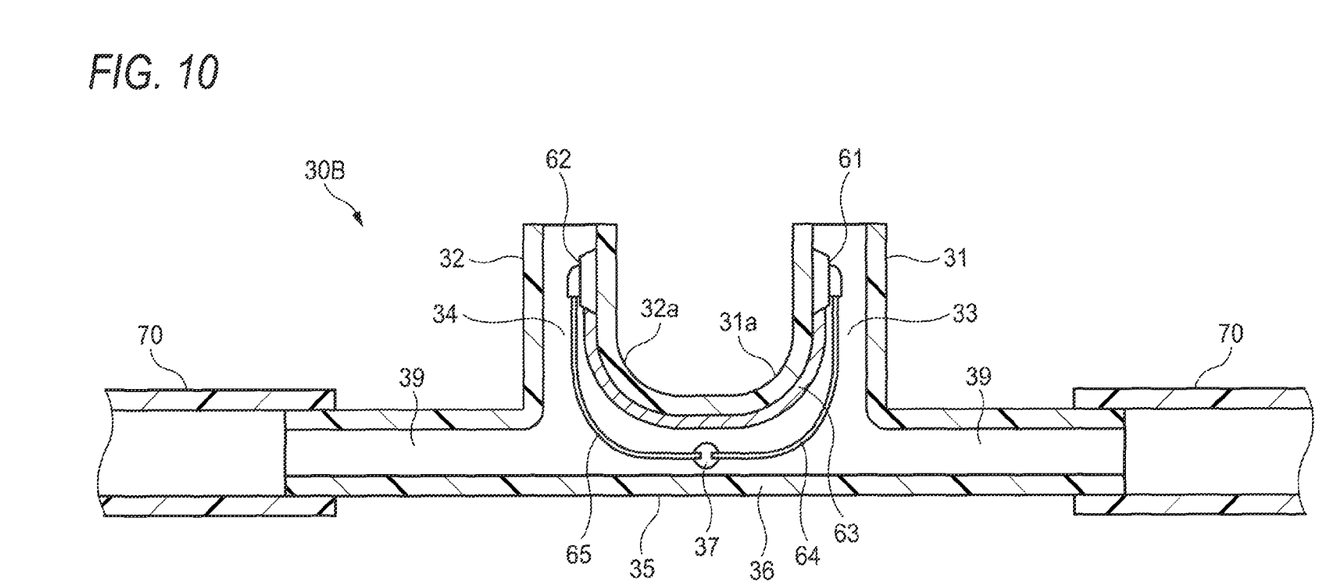
FIG. 10 is a longitudinal sectional view enlargedly illustrating the internal configuration of a nasal tube of the airway adaptor of FIG. 9.

Next, an airway adaptor 10B of a biological information acquiring system 1B of a third embodiment of the presently disclosed subject matter will be described with reference to FIGS. 9 to 11. The components which are identical, similar, or equivalent to those of the airway adaptor 10A of the biological information acquiring system 1A of the second embodiment are denoted by the same reference numerals, and duplicated description is omitted.

Figure 11:
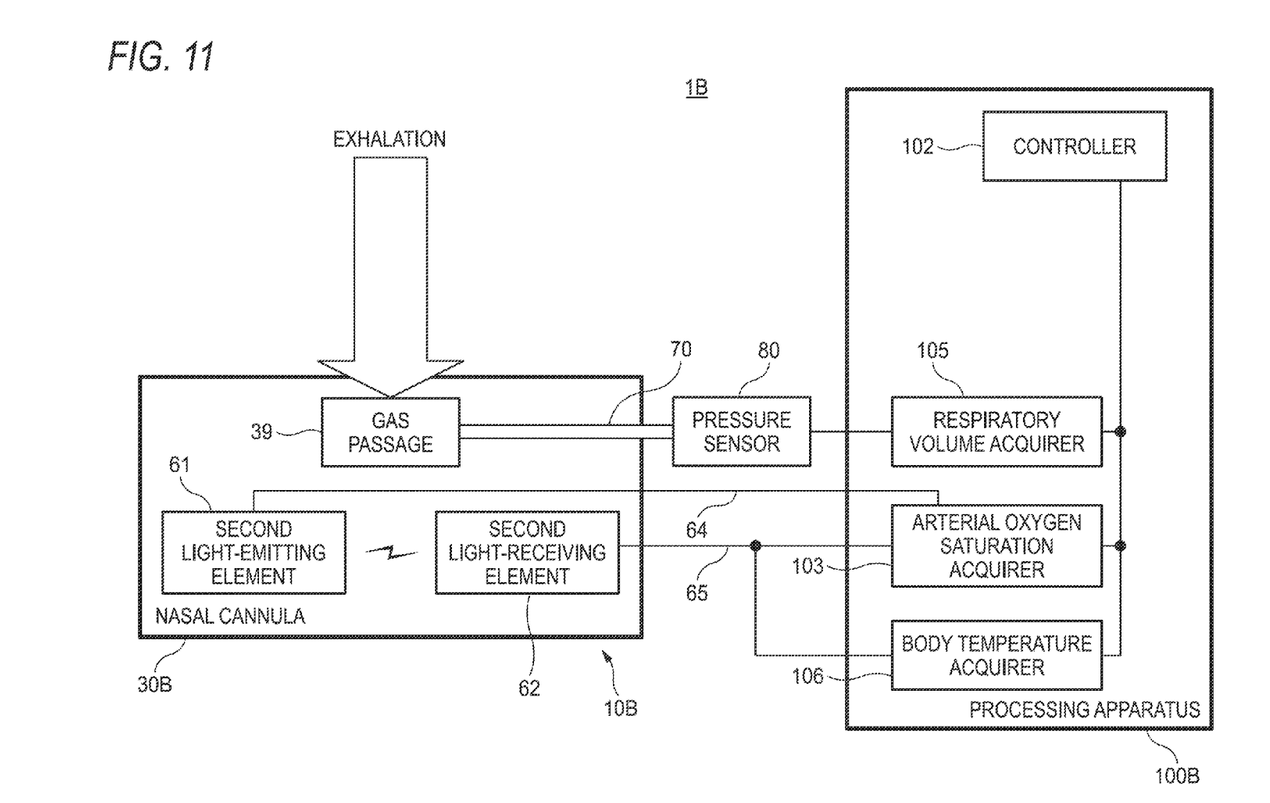
FIG. 11 is a functional block diagram illustrating the configuration of a biological information acquiring system of the third embodiment of the presently disclosed subject matter.

As shown in the functional block diagram of FIG. 11, the biological information acquiring system 1B of the embodiment is different from the biological information acquiring system 1A of the second embodiment in that the configuration for acquiring the concentration of carbon dioxide is not disposed. As shown in FIG. 10, gas passages 39 communicate with the gas passages 33, 34 which are formed in the respective interiors of the insertion portions 31, 32, in the confluent portion 36.

The tubes 70 made of vinyl are detachably attached to the tip ends of the branch gas passages 39, respectively. As shown in FIG. 11, the tubes 70 are connected to the pressure sensor 80. Part of the exhalation from the nostrils 4 of the subject 2 is guided to the pressure sensor 80 through the tubes 70 via the branch gas passages 38. The process which acquires the respiratory volume as biological information, and which is performed by the pressure sensor 80 and the respiratory volume acquirer 105 of the processing apparatus 100A is similar in manner to that in the second embodiment, and hence its description is omitted.

The various kinds of biological information which are acquired by the arterial oxygen saturation acquirer 103, the respiratory volume acquirer 105, and the body temperature acquirer 106 are caused as required to be stored in the storage apparatus (not shown) and/or displayed on the display apparatus (not shown), by the controller 102.

According to the configuration of the embodiment, the placement of the second light-emitting element 61 and second light-receiving element 62 which operate as a part of the arterial oxygen saturation sensor is completed simply by attaching the airway adaptor 10B to the face 3 of the subject 2. Namely, the second light-emitting element 61 and the second light-receiving element 62 are opposed to each other across the nasal septum 4a. The second light-emitting element 61 and the second light-receiving element 62 are supported by the nasal cannula 30B which guides exhalation of the subject 2 to the pressure sensor 80. Although the embodiment can acquire the arterial oxygen saturation, the respiratory volume, and the body temperature as biological information, therefore, the embodiment does not involve labor and botheration of attaching an additional sensor.

Furthermore, the portions 31a, 32a which are in the pair of insertion portions 31, 32, and which are opposed to the nasal septum 4a are caused by the support member 63 to function as a plastically deformable portion. Therefore, the second light-emitting element 61 and the second light-receiving element 62 can be prevented from being separated from the nasal septum 4a, by causing the support member 63 to be deformed so as to extend along the shape of the surface of the nasal septum 4a. According to the configuration, the accuracy of the measurement of the arterial oxygen saturation can be enhanced.

The embodiments have been described in order to facilitate understanding of the invention, and are not intended to limit the invention. It is a matter of course that the invention may be changed or improved without departing the spirit thereof, and includes equivalents thereof.

The second light-emitting element 61 and the second light-receiving element 62 are not always necessary to be placed inside of the gas passages 33, 34 the pair of insertion portions 31, 32. These elements may be placed on the outer circumferential surfaces of the insertion portions 31, 32, respectively, as far as, when the insertion portions 31, 32 are inserted into the nostrils 4 of the subject 2, the insertion portions 31, 32 are disposed at positions where the portions are opposed to each other across the nasal septum 4a.

The support member 63 is not always necessary to be disposed along the inner walls of the portions 31a, 32a of the insertion portions 31, 32 which are opposed to the nasal septum 4a. The member may be disposed along the outer circumferential surfaces of the insertion portions 31, 32, as far as at least the portions 31a, 32a are plastically deformable. Alternatively, a configuration where the member is embedded in the circumferential wall forming the insertion portions 31, 32 may be employed.

The support member 63 is not always necessary to be a wire member. As the support member, appropriate material and shape may be selected, as far as they can cause the portions 31a, 32a of the insertion portions 31, 32 which are opposed to the nasal septum 4a, to be plastically deformable. Moreover, the support member 63 is not always necessary to directly support the second light-emitting element 61 and the second light-receiving element 62, as far as the positions of the second light-emitting element 61 and the second light-receiving element 62 can be maintained.

The biological information acquiring system of the presently disclosed subject matter is requested to acquire at least one kind of biological information in addition to the arterial oxygen saturation. For example, the configuration for causing the second light-receiving element 62 to operate as a part of the temperature sensor may be omitted.

The pressure sensor 80 is not always necessary to be separately disposed outside the processing apparatus 100 (100A, 100B), and may be configured to be incorporated as a part of the processing apparatus 100 (100A, 100B).

In the processing apparatus 100B in the third embodiment, a configuration may be employed where a carbon dioxide sensor is disposed in place of or in addition to the respiratory volume acquirer 105, and the exhalation of the subject 2 flows into the sensor through the tubes 70. In this case, the carbon dioxide concentration in the exhalation of the subject 2 can be acquired as biological information.

According to an aspect of the presently disclosed subject matter, the placement of the carbon dioxide sensor, and that of the light-emitting and light-receiving elements which operate as a part of the arterial oxygen saturation sensor are completed simply by attaching the airway adaptor to the face of the subject. Therefore, it is not necessary to attach the carbon dioxide sensor and the arterial oxygen saturation sensor to respective separate places of the body of the subject. Consequently, the labor of the attaching work can be saved, and botheration felt by the subject can be suppressed.

According to an aspect of the presently disclosed subject matter, the insertion portions of the nasal cannula can be plastically deformed so as to extend along the shape of the surface of the nasal septum, by applying a force to the insertion portions in the state where the light-emitting and light-receiving elements are opposed to each other across the nasal septum. Even after the force application is cancelled, the insertion portions maintain the deformed shape, and therefore the light-emitting and light-receiving elements can be prevented from being separated from the nasal septum. According to the configuration, the accuracy of the measurement of the arterial oxygen saturation can be enhanced.

According to an aspect of the presently disclosed subject matter, in a case where a pressure sensor is further provided and the nasal cannula includes a branch gas passage which is configured to guide a pressure generated by the exhalation from the nostrils to the pressure sensor, the respiratory condition and volume of the subject of the subject can be acquired as biological information without involving labor and botheration of attaching an additional sensor.

According to an aspect of the presently disclosed subject matter, in a case where the light-receiving element operates as a part of a temperature sensor, the respiratory condition and body temperature of the subject can be acquired as biological information without involving labor and botheration of attaching an additional sensor.

According to an aspect of the presently disclosed subject matter, the placement of the nasal cannula for acquiring the respiratory volume, and that of the light-emitting and light-receiving elements which operate as a part of the arterial oxygen saturation sensor are completed simply by attaching the airway adaptor to the face of the subject. Therefore, it is not necessary to attach the nasal cannula and the arterial oxygen saturation sensor to respective separate places of the body of the subject. Consequently, the labor of the attaching work can be saved, and botheration felt by the subject can be suppressed.

According to an aspect of the presently disclosed subject matter, the placement of the nasal cannula for acquiring the concentration of carbon dioxide, and that of the light-emitting and light-receiving elements which operate as a part of the arterial oxygen saturation sensor are completed simply by attaching the airway adaptor to the face of the subject. Therefore, it is not necessary to attach the nasal cannula and the arterial oxygen saturation sensor to respective separate places of the body of the subject. Consequently, the labor of the attaching work can be saved, and botheration felt by the subject can be suppressed.

What is claimed is:

1. An airway adaptor which is adapted to be attached to a face of a subject, the airway adaptor comprising:
   an airway case which includes a gas passage, the airway case adapted to be attachable to a part of a carbon dioxide sensor configured to detect a concentration of carbon dioxide contained in exhalation of the subject, the exhalation flowing into the gas passage, the part of the carbon dioxide sensor including a first light-emitting element and a first light-receiving element;
   a nasal cannula having a pair of insertion portions which are adapted to be inserted respectively into nostrils of the subject to guide exhalation from the nostrils to the gas passage when the airway adaptor is attached to the face;

a mouth guide adapted to be placed in front of a mouth of the subject to guide exhalation from the mouth to the gas passage when the airway adaptor is attached to the face;

a second light-emitting element supported by one of the pair of insertion portions; and a second light-receiving element supported by the other of the pair of insertion portions, wherein when the pair of insertion portions are inserted into the nostrils of the subject, the second light-emitting element and the second light-receiving element are opposed to each other across a nasal septum of the subject, and the second light-receiving element operates as a part of a temperature sensor for acquiring body temperature of the subject.

2. The airway adaptor according to claim 1, wherein at least a part of the pair of insertion portions is elastically deformable, the part being to be opposed to the nasal septum.

3. The airway adaptor according to claim 1, wherein the nasal cannula includes a branch gas passage which is configured to guide a pressure generated by the exhalation from the nostrils to a pressure sensor.

4. A biological information acquiring system comprising:

an airway case which is adapted to be attached to a face of a subject, and which includes a gas passage;

a carbon dioxide sensor which is attached to the airway case, and which is configured to detect a concentration of carbon dioxide contained in exhalation of the subject, the exhalation flowing into the gas passage, the carbon dioxide sensor including a first light-emitting element and a first light-receiving element;

an arterial oxygen saturation sensor which is configured to detect an arterial oxygen saturation of the subject;

a nasal cannula having a pair of insertion portions which are adapted to be inserted respectively into nostrils of the subject to guide exhalation from the nostrils to the gas passage when the airway case is attached to the face;

a mouth guide adapted to be placed in front of a mouth of the subject to guide exhalation from the mouth to the gas passage when the airway case is attached to the face;

a second light-emitting element supported by one of the pair of insertion portions; and a second light-receiving element supported by the other of the pair of insertion portions, wherein when the pair of insertion portions are inserted into the nostrils of the subject, the second light-emitting element and the second light-receiving element are opposed to each other across a nasal septum of the subject to operate as a part of the arterial oxygen saturation sensor, and the second light-receiving element operates as a part of a temperature sensor for acquiring body temperature of the subject.

5. The biological information acquiring system according to claim 4, wherein at least a part of the pair of insertion portions is an elastically deformable portion, the part being to be opposed to the nasal septum.

6. The biological information acquiring system according to claim 4, further comprising:

a pressure sensor, wherein the nasal cannula includes a branch gas passage which is configured to guide a pressure generated by the exhalation from the nostrils to the pressure sensor.

7. A biological information acquiring system comprising:

a pressure sensor;

an arterial oxygen saturation sensor configured to detect an arterial oxygen saturation of a subject;

a nasal cannula having: a pair of insertion portions which are adapted to be inserted respectively into nostrils of the subject; and a gas passage which is configured to guide a pressure generated by exhalation from the nostrils to the pressure sensor, the gas passage communicating with gas passages formed in respective interiors of the pair of insertion portions;

a light-emitting element supported by an interior of one of the pair of insertion portions; and a light-receiving element supported by an interior of the other of the pair of insertion portions, wherein when the pair of insertion portions are inserted into the nostrils of the subject, the light-emitting element and the light-receiving element are opposed to each other across a nasal septum of the subject to operate as a part of the arterial oxygen saturation sensor, at least a part of the pair of insertion portions is formed as an elastically deformable portion, the part being to be opposed to the nasal septum, and the light-receiving element operates as a part of a temperature sensor for acquiring body temperature of the subject.

8. A biological information acquiring system comprising:

a carbon dioxide sensor configured to detect a concentration of carbon dioxide contained in exhalation of a subject, the carbon dioxide sensor including a first light-emitting element and a first light-receiving element;

an arterial oxygen saturation sensor configured to detect an arterial oxygen saturation of the subject;

a nasal cannula having: a pair of insertion portions which are adapted to be inserted respectively into nostrils of the subject; and a gas passage which is configured to guide a pressure generated by exhalation from the nostrils to the carbon dioxide sensor;

a second light-emitting element supported by an interior of one of the pair of insertion portions; and a second light-receiving element supported by an interior of the other of the pair of insertion portions, wherein when the pair of insertion portions are inserted into the nostrils of the subject, the second light-emitting element and the second light-receiving element are opposed to each other across a nasal septum of the subject to operate as a part of the arterial oxygen saturation sensor, and at least a part of the pair of insertion portions is formed as an elastically deformable portion, the part being to be opposed to the nasal septum, and the second light-receiving element operates as a part of a temperature sensor for acquiring body temperature of the subject.

\* \* \* \* \*